United States Patent [19]

Khanna

[11] 4,369,175

[45] Jan. 18, 1983

[54] PROCESS FOR THE MANUFACTURE OF PROLONGED ACTION VINCAMINE PREPARATIONS, THE VINCAMINE PREPARATIONS SO OBTAINED, AND MEDICAMENTS CONTAINING THEM

[75] Inventor: Satish C. Khanna, Bottmingen, Switzerland

[73] Assignee: Ciba-Geigy Corporation, Ardsley, N.Y.

[21] Appl. No.: 288,236

[22] Filed: Jul. 27, 1981

[51] Int. Cl.³ .......................................... A61K 31/795
[52] U.S. Cl. ...................................... 424/79; 525/347
[58] Field of Search .................... 546/51; 424/256, 79; 525/347

[56] References Cited

U.S. PATENT DOCUMENTS

| | | | |
|---|---|---|---|
| 2,990,332 | 6/1961 | Keating | 424/79 |
| 3,313,686 | 4/1967 | Bryan et al. | 424/79 |

FOREIGN PATENT DOCUMENTS

| | | |
|---|---|---|
| 1045599 | 12/1958 | Fed. Rep. of Germany . |
| 2707763 | 9/1977 | Fed. Rep. of Germany . |
| 2179538 | 11/1973 | France . |
| 2201898 | 5/1974 | France . |
| 2253507 | 8/1975 | France . |
| 2313915 | 1/1977 | France . |
| 892083 | 3/1962 | United Kingdom . |
| 925890 | 5/1963 | United Kingdom . |
| 942873 | 11/1963 | United Kingdom . |
| 994918 | 6/1965 | United Kingdom . |
| 1045838 | 10/1966 | United Kingdom . |
| 1191372 | 5/1970 | United Kingdom . |

*Primary Examiner*—Donald G. Daus
*Assistant Examiner*—Diana G. Rivers
*Attorney, Agent, or Firm*—Joseph G. Kolodny

[57] ABSTRACT

The invention relates to a process for the manufacture of prolonged action and stable vincamine preparations, which process comprises reacting an acid addition salt of vincamine with an alkali metal salt or alkaline earth metal salt of a sulfonic acid cation exchange resin, in particular an alkali metal salt of a sulfonated copolymer of styrene with a small amount of divinyl benzene, in a polar reaction medium such as water. The invention further relates to the vincamine preparations so obtained, to the use thereof for the manufacture of ready-for-use medicaments for oral administration and to these medicaments themselves.

12 Claims, No Drawings

PROCESS FOR THE MANUFACTURE OF PROLONGED ACTION VINCAMINE PREPARATIONS, THE VINCAMINE PREPARATIONS SO OBTAINED, AND MEDICAMENTS CONTAINING THEM

The present invention relates to a process for the manufacture of prolonged action vincamine preparations, to the vincamine preparations so obtained, and to medicaments containing these preparations.

Vincamine and the pharmaceutically acceptable acid addition salts thereof in the form of medicaments have met with great interest and are already widely used in practice, especially in geriatry, e.g. for the treatment of cerebral circulatory disturbances and cerebral hypoxia and its sequels. The preferred daily dose of vincamine or its hydrochloride in oral administration is 60 mg, with initial doses of up to 80 mg and maintenance doses from 30 mg. Corresponding dosage unit forms usually contain 10, 15, 20 or, in particular, 30 mg of active ingredient.

In published French patent application No. 2 253 507, A. Houdet has proposed the administration of vincamine or its derivatives by means of prolonged action dosage forms. As such dosage forms there are mentioned and specifically described, in particular, tablets prepared with the aid of carriers which delay the release of the active ingredient, for example carboxypolymethylene, cellulose acetophthalate or palmitostearates of glycerol, as well as gelatin capsules filled with active ingredient granulates and, for intramuscular administration, solutions of acid addition salts of vincamine in polyvinyl pyrrolidone. Further, mention is also made of the use of acid addition salts with reduced solubility, as of the pamoate already described in published French patent application No. 2 179 538, and, finally, the bonding of vincamine on cationic ion exchangers, as possibilities of preparing delayed release dosage forms of active ingredients whose prolonged action is not dependent on the carrier employed; but no further particulars, e.g. regarding types of cation exchangers which can be used and kind of the transformation thereof, are provided. In German Offenlegungsschrift No. 2 707 763, E. Corvi Mora proposes the oral administration of vincamine, or the hydrochloride thereof, for circulatory disorders of the brain, such that a concentration of vincamine in the blood of 0.1 to 0.3 $\mu$g/ml is maintained to achieve a metabolic effect and a concentration of 0.2 to 0.5 $\mu$g/ml is maintained to produce a central vasodilative action. This is accomplished preferably by administering vincamine, or the hydrochloride thereof, in the form of a medicinal preparation with delayed release of the active ingredient, i.e. extending over 24 hours. The delayed release of the active ingredient is effected by coating the active ingredient with a lipid layer or by incapsulating it in a suitable matrix. Such a matrix can consist of polyethylene glycols or ethers thereof, ethyl cellulose or hydroxypropyl cellulose, polymeric metasilicic acid, polyvinyl chloride, polyvinyl acetate, styrene/maleic acid copolymers and natural rubber or mixtures thereof, optionally together with inert fillers. The resultant granulates can be used for the preparation of tablets, capsules, sugar-coated tablets or also liquid suspensions.

Numerous prolonged action preparations containing vincamine, or acid addition salts thereof, are also used as commercial preparations in medical practice, cf. for example "Rote Liste" 1979, preparations 36066B, 36078B, 36084B, 36085B, 36092B, 36093B and 36095B, as well as literature relating to the testing of delayed active ingredient release from such preparations, e.g. Pharm. Ztg. 122, 2067–73 (1977), Dtsch. Apoth. Ztg. 118, 1–4 (1978), Therapiewoche 23, 4709–4714 (1978) and Arzneimittel-Forsch. 28, 2332–6 (1978). Some of the prolonged action commercial preparations for oral administration are capsules, others are tablets or sugar-coated tablets provided with a matrix and/or a coating which ensures the delayed release of active ingredient.

The use of cation exchange resins for the production of prolonged action pharmaceutical preparations from basic active ingredients has, in principle, long been known. For example, German Offenlegungsschrift No. 1 045 599 describes the manufacture of prolonged action amine preparations by reacting therapeutically active amine compounds with sulfonic acid cation exchange resins. These latter are, in particular, sulfonated polyvinyl aryl compounds which are crosslinked with 3–12%, preferably 5–10%, of divinylbenzene, and which are reacted in the form of free acids, e.g. suspended in water/methanol, with amphetamine, pyrilamine or pyribenzamine as bases. In British Pat. No. 857 194, cation or anion exchange resins are combined with at least two basic or two acid therapeutically active ingredients to corresponding combinations. For example, the acid form of a suitable crosslinked polystyrenesulfonic acid resin is reacted with an aqueous solution of an amount of hyoscyamine sulfate insufficient for saturation and subsequently with an aqueous solution of hyoscine hydrobromide.

Apart from the mention in French patent application No. 2 179 538 referred to above, no further regard has been paid to or any practical use made of the bonding of vincamine on any cation exchange resins. This may be because the vincamine resinates formed direct from sulfonic acid and cation exchange resins and vincamine are not stable. Our own findings made by thin-layer chromatography or liquid chromatography show that the crude base which is set free again subsequent to the reaction with the cation exchanger from this latter by pulverising the resinate, allowing it to swell in aqueous sodium acetate solution and chloroform, then heating the mixture to 60° C. under reflux and thereafter separating and evaporating the chloroform phase, contains at least 10% of apovincamine and about 5% of epivincamine. This instability results in a decrease in the activity and in a change in the pharmacological properties.

Surprisingly, it has now been found that prolonged action and stable vincamine preparations are obtained by reacting an acid addition salt of vincamine with an alkali metal salt or alkaline earth metal salt of a sulfonic acid cation exchange resin, in a polar reaction medium.

Suitable acid addition salts of vincamine are both those with inorganic acids and with organic acids. Particularly suitable are addition salts with mineral acids, especially with hydrohalic acids, e.g. hydrochloric acid, and also with sulfuric acid, and with organic sulfonic acids such as methanesulfonic acid, and with carboxylic acids, e.g. tartaric acid, succinic acid or acetic acid.

In principle, all sulfonic acid cation exchange resins in the form of their alkaline earth metal salts and, in particular, of their alkali metal salts, are suitable for the reaction of this invention. Bby sulfonic acid cation exchange resins are meant, in addition to those without other functional groups than sulfo groups, also phenolsulfonic acid cation exchange resins and carboxylic acid-sulfonic acid cation exchange resins, as well as those containing further functional groups. Particularly satisfactory results are obtained with sulfonation products of copolymers of styrenes which are unsubstituted or substituted by inert groups and small amounts of divinyl benzenes as crosslinking agents such as those described in U.S. Pat. No. 2,366,007. Examples of other suitable cation exchange resins are condensation products of phenols or phenol ethers with formaldehyde and unsubstituted or substituted benzenesulfonic acids, or condensation products of formaldehyde with aromatic sulfonic acids substituted by free or etherified hydroxy, such as the condensation products of formaldehyde with naphthalenesulfonic acids and phenoxyacetic acids, or of formaldehyde with the triphenylmethane derivatives obtained by condensation of benzaldehydedisulfonic acids with two molecules of phenoxyacetic acid, which condensation products are described as carboxylic acid-sulfonic acid cation exchange resins in U.S. Pat. Nos. 2,729,607 and 2,692,866, as well as further cation exchange resins described in U.S. Pat. Nos. 2,204,259 and 2,338,159.

The resins employed can be uncrosslinked; however, it is preferred to use resins having a degree of crosslinking from about 1 to 12%, preferably from 4 to 8%. The particle size of the resins employed is preferably from about 50 to 1000 $\mu$m and, in particular, e.g. of sulfonated polystyrene crosslinked with divinyl benzene, from about 100 to 300 $\mu$m. The rate of release of active ingredient decreases with increasing degree of crosslinking and with increasing particle size, for which reason it is possible to maintain a desired rate of release using resins of different particle size by modifying the degree of crosslinking, e.g. by using a resin of the type specified above having a particle size of 150–300 $\mu$m and a degree of crosslinking of 4% for preparing solid forms for oral administration, or having a particle size of 50–100 $\mu$m and a degree of crosslinking of 8% for the preparation of suspensions for oral administration.

Examples of suitable polar reaction media for the reaction of the present invention are water and polar organic solvents such as monovalent lower alkanols, e.g. methanol or ethanol, or lower alkanones, e.g. acetone, or mixtures of these solvents with each another and/or with water.

In order to keep the amount of cation exchange resin and total weight and volume of the finished preparations low, it is possible in the reaction of the invention to effect as high a saturation as possible of the cation exchange resin by appropriate choice of the proportions of acid addition salt of vincamine and alkali metal or alkaline earth metal salt of the cation exchange resin. The degree of saturation is usually from about 10% to 40% and, aside from the proportions, it depends also on the resin employed and on the reaction conditions. The remaining sulfonic acid anions are substantially saturated by alkali metal and alkaline earth metal ions. The reactions are preferably conducted, with stirring, at room temperature or in the range from 20° to 60° C., most preferably at about 40° C. The reaction times are from about 5 to 15 hours. When using resins having a low degree of crosslinking or those having a smaller particle size, the reaction time is closer to or also less than 5 hours, otherwise closer to or also longer than 15 hours. The reaction products can be worked up in simple manner by filtration and drying, preferably to constant weight, e.g. in vacuo in the temperature range up to about 80° C., preferably at about 50° C.

The vincamine preparations obtained by the process of the invention, also referred to hereinafter as vincamine resinates, are very stable, in contrast to the vincamine resinates obtained by direct reaction of vincamine with acid cation exchange resins and referred to above. The vincamine contained in a vincamine resinate of this invention (obtained from a sulfonated copolymer of styrene and divinyl benzene and having a degree of crosslinking of 4%) was still virtually unchanged after six months' storage at 23° C., at 35° C. and even at 50° C. The rate of active ingredient release was also almost unchanged after these storage tests. This latter is also surprisingly little dependent on the pH value of the ambient liquid: using a resinate employed in the practice of this invention and obtained from a cation exchange resin of the type specified above, but having a degree of crosslinking of 8% and a particle size of 150–300 $\mu$m, the amount of active ingredient released in a simulated gastric juice of pH 1.2 over 4 hours corresponded to the amount of active ingredient released in simulated intestinal juice of pH 7.5 over 6 hours. For this reason, release tests with resinates obtained from resins of the same type and having degrees of crosslinking of 4%, 6% and 8%, with one hour sojourn time in the simulated gastric juice and 7 hours sojourn time in the intestinal juice, show unbroken release curves (axis of abscissa: time, axis of ordinate: liberated amount of vincamine expressed as percentage of the total content).

The vincamine preparations obtained in the practice of this invention can be administered, as such, orally; preferably, however, they are used in analogous manner to crystallised active ingredients, or active ingredients solidified in some other manner, for the manufacture of customary dosage forms of medicaments for oral administration. For example, they are processed in conventional manner and with customary carriers and excipients to solid dosage forms, e.g. tablets, including special forms such as film-coated tablets or inlay tablets, to sugar-coated tablets or capsules, as well as to liquid dosage forms for oral administration, especially to syrups, i.e. aromatised suspensions, and also to drop suspensions. The dosage can be the usual one or also slightly reduced or increased. Accordingly, the vincamine concentration of the individual dosage units can correspond to half the daily dose or, with correspondingly delayed release of the active ingredient, which can be further reduced by conventional delaying methods such as the use of appropriate matrixes, to a whole daily dose, and therefore can be from 15 to 30 mg or 30 to 60 mg, and also up to 100 mg.

The following Examples describe the manufacture of vincamine resinates employed in the practice of this invention and of ready-for-use dosage forms containing these resinates, but in no way limit the scope of the invention.

EXAMPLE 1

(a) Preparation of the resin 1 kg of Zerolit 225-Na (registered trademark of Diaprosim Ltd., England; sulfonated copolymer of styrene and divinyl benzene with 4% crosslinking and a particle size of 150–300 $\mu$m, average particle size 225 $\mu$m) are suspended in about 5 liters of 2 N hydrochloric acid, and the mixture is stirred for 2 hours at 40° C. The supernatant solution is decanted and the resin is washed 3 times with deionised water. Then 5 liters of 2 N sodium hydroxide are added and the mixture is stirred for 6 hours at 40° C. The resin is rinsed with excess hot deionised water until the pH of the wash solution is almost 5. These process steps are repeated twice in order to ensure a good quality of the resin. Finally, the resin is suspended for 2 hours in isopropyl alcohol to remove any organic impurities. The resin is then separated by filtration and washed with two portions of deionised water. It is then dried to constant weight at 50° C. in vacuo.

(b) Loading the resin with vincamine 100 g of vincamine methanesulfonate are dissolved in 1 liter of deionised water. Then 365 g of the activated resin obtained in accordance with the above particulars are slowly dispersed in this solution. The mixture is then stirred at 40° C. until all the active ingredient is bound on the resin. The residual concentration of the vincamine salt in the solution is kept under observation by UV spctrophotometry. The vincamine resinate is collected by filtration and dried to constant weight in vacuo at 50° C.

(c) Preparation of a dosage form for oral administration 100 g of the dried vincamine resinate are mixed with 1 g of magnesium stearate and filled into capsules, such that each capsule has a vincamine content corresponding to 100 mg of vincamine hydrochloride.

EXAMPLE 2

(a) Preparation and loading of the resin 80 g of Amberlite IRP 69 M (sulfonated copolymer of styrene containing about 8% of divinylbenzene, Rohm+Haas Co., Philadelphia) having a particle size smaller than 75 μm are prepared as described in Example 1. A warm solution of 50° C. containing 20 g of vincamine hydrochloride in 1 liter of deionised water is added to the wet resin. The resultant suspension is stirred at 50° C. for 24 hours. The treated resin material is collected by filtration and dried in vacuo at 50° C. The dried resinate contains vincamine in an amount corresponding to a content of 20% by weight of vincamine hydrochloride.

(b) Preparation of a dosage form for oral administration 4 g of tragacanth, 1.2 g of p-hydroxybenzoic acid methyl ester and 0.3 g of p-hydroxybenzoic acid propyl ester are dissolved in 1 liter of water at 80°–90° C. The resultant gel is cooled and 50 g of the above dried vincamine resinate are added and thoroughly dispersed using a homogeniser. The dispersion is then bulked with water to a final volume of 1 liter, such that the resultant suspension contains about 5% of vincamine resinate. One teaspoonful of this suspension contains a dose corresponding to about 50 mg of vincamine hydrochloride. Exactly this dose is contained in 2.5 ml of suspension.

EXAMPLE 3

1 kg of the dry vincamine resinate obtained in Example 2 is mixed with 0.5 kg of lactose and 0.5 kg of maize starch and the mixture is kneaded with 0.5 liter of 15% mucilage of polyvinyl pyrrolidone and then granulated. The granulate is dried, mixed with 0.02 kg of aerosol (highly dispersed silica gel) and 0.02 kg of magnesium stearate as outer phase and compressed to 500 mg tablets (diameter of die 11.5 mm). The tablets contain vincamine in a dose corresponding to about 46 mg of vincamine hydrochloride.

What is claimed is:

1. A process for the manufacture of prolonged action and stable vincamine resinates, which process comprises reacting an acid addition salt of vincamine with an alkali metal salt or alkaline earth metal salt of a sulfonic acid cation exchange resin, in a polar reaction medium.

2. A process according to claim 1, which comprises the use of an alkali metal salt or alkaline earth metal salt of a sulfonic acid cation exchange resin having a particle size of about 50 to 1000 μm.

3. A process according to claim 1, wherein an acid addition salt of vincamine is reacted with an alkali metal salt of a sulfonation product of a copolymer of (unsubstituted or substituted) styrene with a small amount of divinyl benzene.

4. A process according to claim 1, wherein the reaction is carried out in water, a lower alkanol, a lower alkanone or a mixture of these solvents with each other and/or with water.

5. A process according to claim 1, wherein the acid addition salt of vincamine is a mineral acid salt or a salt with an organic sulfonic acid.

6. A process according to claim 1, wherein the acid addition salt of vincamine is vincamine methanesulfonate or vincamine hydrochloride.

7. A prolonged action and stable vincamine preparation consisting of vincamine resinate which is bound with a saturation of 10 to 40% on a sulfonic acid cation exchange resin as prepared by the process of claim 1, the remaining sulfonic acid anions of which are substantially saturated by alkali metal or alkaline earth metal ions and an inert pharmaceutical carrier.

8. A vincamine preparation according to claim 7, in which vincamine is bound on a sulfonic acid cation exchange resin having a particle size of about 50 to 1000 μm.

9. A vincamine preparation according to claim 7, in which vincamine is bound on a sulfonation product of a copolymer of unsubstituted or substituted styrene with a small amount of divinyl benzene.

10. A vincamine resinate obtained according to claim 1.

11. A vincamine resinate obtained according to claims 1 or 2.

12. A vincamine resinate obtained according to any one of claims 1, 2, 3, 4 or 5.

* * * * *